United States Patent
Nishimura et al.

(10) Patent No.: US 7,132,506 B2
(45) Date of Patent: Nov. 7, 2006

(54) PEPTIDE HAVING OSTEOGENETIC ACTIVITY AND OSTEOGENETIC ACCELERATOR CONTAINING THE SAME

(75) Inventors: Yoshihiko Nishimura, 25, Kitashirakawa Nishisenouchi-cho, Sakyo-ku, Kyoto-shi, Kyoto 606-2855 (JP); Yoshihisa Suzuki, 38-4-301, Kitashirakawa Oiwake-cho, Sakyo-ku, Kyoto-shi, Kyoto 606-8224 (JP); Masao Tanihara, A-206, 8916-5, Takayama-cho, Ikoma-shi Nara 630-0101 (JP)

(73) Assignees: Kyocera Corporation, Kyoto (JP); Yoshihiko Nishimura, Kyoto (JP); Yoshihisa Suzuki, Kyoto (JP); Masao Tanihara, Nara (JP)

(*) Notice: Subject to any disclaimer, the term of this patent is extended or adjusted under 35 U.S.C. 154(b) by 653 days.

(21) Appl. No.: 10/233,284

(22) Filed: Aug. 30, 2002

(65) Prior Publication Data

US 2003/0082784 A1  May 1, 2003

(30) Foreign Application Priority Data

Aug. 31, 2001 (JP) ............................. 2001-264166

(51) Int. Cl.
*A61K 38/07* (2006.01)
*A61K 38/08* (2006.01)
*A61K 38/10* (2006.01)
*A61K 38/16* (2006.01)
*C07K 7/04* (2006.01)

(52) U.S. Cl. .................... 530/324; 514/12; 514/13; 514/15; 514/18; 530/326; 530/328; 530/330

(58) Field of Classification Search ............ 514/2, 514/12, 13, 14, 15, 18; 530/300, 324, 326, 530/327, 328, 330, 345
See application file for complete search history.

(56) References Cited

U.S. PATENT DOCUMENTS

| | | | |
|---|---|---|---|
| 5,229,490 A | * | 7/1993 | Tam .......................... 530/324 |
| 5,955,584 A | * | 9/1999 | Ditlow et al. ............ 530/388.2 |
| 6,617,307 B1 | | 9/2003 | Nishimura et al. ........... 514/13 |
| 2002/0120103 A1 | * | 8/2002 | Rosen et al. ................ 530/350 |

OTHER PUBLICATIONS

John M. Wozney, et al., "Novel Regulators of Bone Formation: Molecular Clones and Activities", Science vol. 242, pp. 1528-1534, (1990).
Elizabeth A Wang, et al., "Recombinant Human Bone Morphogenetic Protein Induces Bone Formation", Proc. Natl. Acad. Sci. USA, pp. 2220-2224 (1990).
Molecular Medicine vol. 30, No. 10 (1993).
Sequel to Biochemical Experiments 2, Chemistry about Protein (the second volume) May 20, 1987.
E. Atherton, et al., "Solid Phase Peptide Synthesis", pp. 149-157, (1989).
Yoshihisa Suzuki, et al., "Evaluation of a Novel Alginate Gel Dressing: Cytotoxicity to Fibroblasts in Vitro and Foreign-Body Reaction in Pig Skin in Vitro", J. Biomed Mater Res, 39, pp. 317-322, (1998).
Klaus Mosbach, "Immobilized Enzymes and Cells", Method in Enzymology, vol. 135, pp. 30-65, (1987).
Suzuki, et al., "Alginate Hydrogel Linked with Synthetic Oligopeptide Derived from BMP-2 Allows Ectopic Osteoinduction in Vivo." Journal of Biomedical Materials Research. United States, Jun. 5, 2000 pp. 405-409.
Database EMBL Online, Oct. 1, 1989.

* cited by examiner

*Primary Examiner*—Jeffrey Edwin Russel
(74) *Attorney, Agent, or Firm*—Hogan & Hartson, LLP

(57) ABSTRACT

A peptide has at least an amino acid sequence represented by SEQ ID NO:1 and it has an osteogenetic activity.

7 Claims, No Drawings

PEPTIDE HAVING OSTEOGENETIC ACTIVITY AND OSTEOGENETIC ACCELERATOR CONTAINING THE SAME

CROSS-REFERENCE TO RELATED APPLICATION

This application is related to Japanese application No. 2001-264166 filed on Aug. 31, 2001, whose priority is claimed under 35 USC §119, the disclosure of which is incorporated by reference in its entirety.

BACKGROUND OF THE INVENTION

1. Field of the Invention

The present invention relates to a peptide having osteogenetic activity and an osteogenetic accelerator containing the same as an active ingredient.

The peptide and osteogenetic accelerator containing the same as an active ingredient provided by the present invention, which have the osteogenetic activity, is useful for treatment of fractures, for inhibition of decrease in bone substance related to osteoporosis and periodontic diseases, and for prevention of fractures associated with osteoporosis and rheumatoid arthritis and the like.

2. Description of Related Art

Bone morphogenetic protein (BMP) is a member of the transforming growth factor (TGF) β family (Wozney, J. M. et al, Science, 242, 1528 (1988)), and its active form exists as a homodimer having a molecular weight of about 18 kD. BMP has the function of acting on undifferentiated mesenchymal cells, inducing differentiation to chondroblasts and osteoblasts and effecting chondrogenesis and osteogenesis (Wang, E. A. et al. Proc. Natl. Acad. Sci. USA, 87, 2220 (1990)). For this reason, BMP is expected to be effective in treatment of fractures, inhibition of decrease in the bone substance related to osteoporosis and periodontic diseases, and in prevention of fractures associated with osteoporosis and rheumatoid arthritis and the like.

However, the above-described BMP is not absorbed in an effective amount internally when it is administered orally or endermatically, and disappears from blood or tissue within a few minutes when it is administered directly into blood vessels and tissue. However, if administered in a large amount, BMP might possibly cause various adverse effects, including toxic effects on livers and kidneys. Further, BMP has immunogenicity because of its large molecular weight, and might possibly cause anaphylactic shock when administered repeatedly. Furthermore, where BMP is impregnated in matrices of decalcificated bone or collagen for use, osteogenetic activity is expressed, but there may be another problem of antigenicity or infection attributed to the matrices.

SUMMARY OF THE INVENTION

After earnest study with the object of providing a peptide having the osteogenetic activity with the above-mentioned adverse effects reduced, the inventors of the present invention have found that a peptide variant derived from BMP has osteogenetic activity similar to the osteogenetic activity of BMP and accomplished the invention.

According to the present invention, the above-mentioned object is achieved by a peptide having at least an amino acid sequence represented by SEQ ID NO:1 in the sequence listing.

Also the object of the present invention is achieved by an osteogenetic accelerator containing an effective amount of the above-mentioned peptide.

These and other objects of the present application will become more readily apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

DESCRIPTION OF THE PREFERRED EMBODIMENTS

The peptide of the present invention may optionally have addition of one or more amino acids so long as it has at least the amino acid sequence SEQ ID NO:1 exhibiting the osteogenetic activity.

More particularly, the sequence SEQ ID NO:1 may be combined with SEQ ID NO:2, with SEQ ID NO:3 or with both SEQ ID NO:2 and SEQ ID NO:3.

Here, each of SEQ ID NO:1 to SEQ ID NO:3 has an N terminal and a C terminal at its left and at its right, respectively, according to the conventional notation. However, in the combination of SEQ ID NO:1 and SEQ ID NO:2, for example, two orientations are possible, i.e., N terminal-KIPKA . . . STLY-C terminal and N terminal-STLY . . . KIPKA-C terminal. Thus the order of SEQ ID NO:1, SEQ ID NO:2 and SEQ ID NO:3 in the orientation of a whole sequence resulting from combination is not particularly limited. Any orientation that can be conceived about their combination by the conventional method is within the scope of the present invention.

In the above-mentioned combination, one to ten residues of amino acids may intervene between the sequences of SEQ ID NO:1 to SEQ ID NO:3 and/or toward each terminal of the resulting sequence as a whole from the sequence of SEQ ID NO:1, SEQ ID NO:2 or SEQ ID NO:3. Such sequences are within the scope of the present invention. The amino acids may be any amino acids so long as they do not inhibit the osteogenetic activity of the SEQ ID NO:1, and the amino acids may be selected from the group consisting of Asn, Cys, Pro, Gly, Ala, Val, Leu, Ile, Ser, Thr, Glu, Asp, Lys and Tyr. The amino acids may be the same or different.

However, in any combination, SEQ ID NO:1 is preferably located at the C terminal of the resulting sequence, and examples of such combinations suitably used are represented by SEQ ID NO:4 to SEQ ID NO:7.

In the present invention, to "have the osteogenetic activity" may be construed as activity of accelerating the activation of alkaline phosphatase in osteoblasts (Yamaguchi, A., Molecular Medicine, Vol.30, No.10, 1232 (1993)) so as to form neogenetic bone or induce growth of existing bone.

The peptides of the present invention may be prepared by a method usually used for synthesizing peptides, for example, by a solid phase synthesis method or by a liquid phase synthesis method. The solid phase synthesis method is simpler in operation (for example, see "Sequel to Biochemical Experiments 2, Chemistry about Protein (the second volume)" p.p.641–694 edited by the Biochemical Society in Japan published on May 20, 1987 by Tokyo Kagaku Dojin, Japan and "Solid Phase Peptide Synthesis—A Practical Method" p.p.152–154 by Atherton, E. et al. published in 1989 by IRL Press, Oxford). The solid phase synthesis can be carried out usually by protecting amino groups with appropriate protecting groups, for example, either Boc (tert-butoxycarbonyl) or Fmoc (9-fluorenylmethyloxycarbonyl), or a combination thereof.

For preparing the peptide of the present invention by the solid phase synthesis method, for example, with use of a polymer insoluble to a reaction medium, 1) an amino acid corresponding to the C terminal of a target peptide is bound to the polymer via an α-COOH group of the amino acid; 2) subsequently, in the direction to the N terminal of the target peptide, a corresponding amino acid or peptide fragment is bound by condensation to the amino acid after protecting other functional groups such as an α-amino group of the corresponding amino acid or peptide fragment other than an α-COOH group; 3) a protecting group of an amino group forming a peptide bond such as an α-amino group is removed from the bound amino acid or peptide fragment; these steps are repeated to elongate a peptide chain in order to form a peptide chain corresponding to the target peptide.

The thus produced peptide chain is detached from the polymer and protecting groups are removed from protected functional groups to obtain the target peptide, which can be purified suitably.

Here, as the polymer, styrene-divinyl benzene copolymers, Merrifield resins, chloromethyl resins, Wang resins, Sieber resins, rink amide resins, rink acid resins, 2-chlorotrityl chloride resins, HMBA-MBHA resins, MBHA resins, oxime resins and the like may be used. Among these resins, styrene-divinyl benzene copolymers are preferred.

It is preferred from the viewpoint of preventing side reaction that the detachment of the peptide chain from the polymer and the removal of the protecting groups are carried out simultaneously using trifluoroacetic acid or hydrogen fluoride.

As a solvent and a condensing agent in the peptide synthesis, any ones usually known in the art may be used as required. For example, DMF (dimethylformamide), trichloroethanol, N-methylpyrrolidone and the like may be mentioned as solvents, and DCC, HATU (0-(7-azabenzotriazole-1-yl)-1,1,3,3-tetramethyl uronium hexafluorophosphate), HOBt (1-hydroxybenzotriazole), HBTU (0-benzotriazole-1-yl-N,N,N',N'-tetramethyl uronium hexafluorophosphate), PyBOP (benzotriazole-1-yl-oxy-tris-pyrrolidinophosphonium hexafluorophosphate), $CF_3$—$NO_2$-PyBOP and the like may be mentioned as condensing agents.

For purifying the obtained peptide, it is effective to utilize reverse phase liquid chromatography.

Either or both of the N terminal and C terminal of the above-prepared peptide of the present invention may optionally be modified chemically. For example, the N terminal may be acetylated and the C terminal may be amidated or esterified.

The peptide of the present invention may form a physiologically acceptable salt by conventional salt formation reaction. Such salts can include salts with acids such as an inorganic acid (e.g. hydrochloric acid, sulfuric acid and phosphoric acid) or an organic acid (e.g., lactic acid, tartaric acid, maleic acid, fumaric acid, oxalic acid, malic acid, citric acid, oleic acid and palmitic acid); salts with hydroxides and carbonates of alkali metals and alkali earth metals such as sodium, potassium, calcium and aluminum; and salts with amines such as triethylamine, benzylamine, diethanolamine, t-butylamine, dicyclohexylamine and arginine.

The peptide of the present invention has the osteogenetic activity and exhibits low toxicity in toxicity tests.

Therefore, for the purpose of bone formation, the peptide of the present invention may be used as an osteogenetic accelerator independently or as an osteogenetic accelerator obtained by attaching the peptide to a suitable carrier optionally containing pharmacologically acceptable additives such as a stabilizer, a preservative, a thickener, a solubilizer and the like or obtained by solving or suspending the peptide in an aqueous solvent. It is particularly preferable that the osteogenetic accelerator of the present invention comprises the peptide attached to a carrier.

The carrier is preferably biodegradable and bioabsorbable, and for example, it is possible to use, singly or in combination of two or more, various types of ceramic, gels of polysaccharides such as covalently crosslinked gels of alginate (Suzuki, Y. et al., J. Biomed. Mater. Res., 39, 317(1998)) and gels of protein such as collagen.

Among these carriers, gels of polysaccharides are preferred from the view point of non-inflammatory and non-immunogenic properties. The peptide can be attached to the carrier by means of a covalent bond, an ionic bond, a hydrophobic bond, a hydrogen bond, an SS bond and the like, which bonds are formed by immersion, spray, application, dropping or the like with use of a solution of the peptide in dimethylformamide or the like.

The attachment of the peptide by the covalent bond is preferred from the viewpoint of stability and continuity of effect. Such attachment can be done by a method usually used for attaching a physiologically active protein such as an enzyme (for example, see Scouten, W. H., Methods in Enzymol., 135, Mosbach, K. Ed., 1987, Academic Press NY, p.p.30–65).

The thus obtained solid osteogenetic accelerator may be used for implantation in a defective site in bone.

As aqueous solvents used for preparation of a liquid osteogenetic accelerator, may be mentioned physiological saline and physiologically acceptable aqueous solutions of mannitol, sucrose, lactose, maltose, glucose, fructose or the like. A 5% glucose aqueous solution and a physiological saline are preferable.

The osteogenetic accelerator obtained by dissolving or suspending the peptide in the aqueous solvent may be used by intravenous, subcutaneous, intraperitoneal, intra-articular or dermal administration or by filling it in a defective site in bone according to the type of its formulation. Further, if capsulated or made into liposomes by the conventional method, the osteogenetic accelerator can be administered orally.

The peptide and the osteogenetic accelerator of the invention can promote treatment of fractures by being administered to patients with fractures caused by external causes, rheumatoid arthritis and osteoporosis or by being filled or implanted in a fracture site in bone.

Also they can suppress decrease in bone substance due to osteoporosis and periodontic diseases and prevent fractures due to osteoporosis and rheumatoid arthritis by being administered to patients with osteoporosis, periodontic diseases and rheumatoid arthritis.

The dose of the peptide of the present invention may vary as required depending upon the weight of bone desired to be formed, the site of injured bone, the condition of bone, and the age, sex and weight of a patient and the like. But usually, the peptide expresses its osteogenetic activity by being administered or implanted as an active ingredient at a dose of 0.01 μg/kg to 2 g/kg (for an adult), preferably 0.01 μg/kg to 200 mg/kg (for an adult).

EXAMPLES

The present invention is now described by way of examples, which should not be construed to limit the scope of the invention.

Example 1

A peptide having the amino acid sequence SEQ ID NO:4 which had an amino group at the N terminal and a carboxyl group at the C terminal was synthesized by the solid phase synthesis method using an automatic peptide synthesizer.

More particularly, with use of 0.1 mmol of particulate resin (produced by US Applied Biosystems, HMP leucine) comprised of styrene-divinylbenzene copolymer (the molar composition ratio of styrene to divinylbenzene was 99:1) containing 4-(Nα-9-(fluorenylmethoxycarbonyl)-L-leucyl)-oxymethyl-phenoxy-methyl group in a proportion of 0.74 mmol/g-resin, successively bound were amino acids corresponding in the direction from the carboxyl terminal to the amino terminal of the target peptide. In binding reaction, used as amino acids were Nα-9-(fluorenylmethoxycarbonyl)-N β-trityl-L-asparagine (Fmoc asparagine), Nα-9-(fluorenyl-methoxycarbonyl)-0-t-butyl-L-serine (Fmoc serine), Nα-9-(fluorenylmethoxycarbonyl)-valine (Fmoc-valine), Nα-9-(fluorenylmethoxycarbonyl)-Nε-t-butyloxycarbonyl-L-lysine (Fmoc lysine), Nα-(fluorenylmethoxycarbonyl)-L-isoleucine (Fmoc isoleucine), Nα-(fluorenylmethoxycarbonyl)-L-proline (Fmoc proline), Nα-(fluorenylmethoxycarbonyl)-L-alanine (Fmoc Alanine), Nα-9-(fluorenylmethoxycarbonyl)-S-trityl-L-cysteine (Fmoc cysteine), Nα-9-(fluorenylmethoxycarbonyl)-0-t-butyl-L-threonine (Fmoc threonine), Nα-9-(fluorenylmethoxycarbonyl)-β-butyl-L-glutamic acid (Fmoc glutamic acid), Nα-(fluorenylmethoxycarbonyl)-L-leucine (Fmoc leucine), and Nα-(fluorenylmethoxycarbonyl)-0-t-butyl-L-thyrosin (Fmoc thyrosin), all being produced by US applied Biosystems, in an amount of 1 mmol in each binding step.

HBTU and HOBt were used for producing the bonds of the amino acids.

The resulting peptide resin was treated with 10 ml of trifluoroacetic acid containing 2.5% of water and 2.5% of ethanedithiol for three hours. The resulting solution was added to diethyl ether. The generated precipitate was further washed with diethyl ether several times in order to deprotect the peptide and detach it from the resin. The resulting crude product was purified by preparative Reverse Phase High Performance Liquid Chromatography (column: Novapak HR C18 25×100 mm, RCM 25×10 with a pressure module produced by Nippon Waters Kabushiki Kaisha, Japan).

The resulting purified peptide was subjected to an AKTA explorer 10XT produced by Pharmacia Biotech Kabushiki Kaisha, Japan (column: Novapak C18 3.9×150 mm produced by Nippon Waters Kabushiki Kaisha, mobile phase: a mixture solvent of water and acetonitrile containing 0.05 vol % of trifluoroacetic acid (with varying the concentration of acetonitrile from 5 vol % to 50 vol % in 30 minutes), a flow rate: 1 mL/min.). A single peak was observed at 21.6 min. The molecular weight of the purified peptide was found to be 2,637 by FAB mass spectrometry (theoretical molecular weight 2,636.06).

Examples 2 to 5

Peptides (Examples 2 to 4) having the amino acid sequences SEQ ID NO:4, SEQ ID NO:5 and SEQ ID NO:6, respectively, and having an amino group at the N terminal and an amide group at the C terminal, and a peptide (Example 5) having the sequence SEQ ID NO:7 and having an amino group at the N terminal and an amide group at the C terminal were synthesized in the same manner as in Example 1, except that used were 0.1 mmol of particulate resin (produced by US Applied Biosystems, Fmoc amide resin) comprised of styrene-divinylbenzene copolymer (the molar composition ratio of styrene to divinylbenzene was 99:1) containing 4-(2',4'-dimethoxyphenyl-fluorenyl-methoxycarbonyl-aminoethyl )phenoxyacetoamide-ethyl group in a proportion of 0.62 mmol/g-resin.

The resulting peptide resins were subjected to deprotection and detachment from the solid phase and the resulting crude products were purified, in the same manner as in Example 1.

The purified peptides were each examined on elution time and molecular weight by analytical HPLC and by FAB mass spectroscopy, respectively. The results are shown in Table 1.

TABLE 1

| Examples | Elution Time | Molecular Weight | Theoretical Molecular Weight |
|---|---|---|---|
| Example 2 | 22.0 mm | 2636 | 2635.08 |
| Example 3 | 21.4 mm | 2596 | 2619.01 |
| Example 4 | 21.7 mm | 2604 | 2117.51 |
| Example 5 | 13.8 mm | 595 | 594.71 |

Test Example 1

Induction of Alkali Phosphatase Activity in C3H10T1/2 Cell Strain

Undifferentiated mouse mesenchymal cell strain C3H10T1/2 (purchased from Dai-Nippon Seiyaku KK, Japan) was dispersed in Eagle's MEM medium containing 10% of fetal bovine serum in a cell concentration of 3.75× $10^4$ cells/mL, and thus a cell culture liquid was prepared. The cell culture liquid was distributed by 100 μL in each well of the 96-hole plates, on which the peptides of Examples 1 to 5, 200 μg each, had been solidified by air drying, and incubated at 37° C. in the presence of 5% $CO_2$.

As a control, the cells are distributed in the same number into wells without any peptide solidified, and thereafter 50 ng of human recombinant BMP-2 (R&D Systems, Inc.) were added. Also blank wells were prepared to which neither human recombinant BMP-2 nor the solidified peptides were added.

Three days after the start of incubation, a culture supernatant was removed, and the wells were washed once with phosphate buffer (PBS: 10 mM, containing 0.15 M of common salt, pH 7.4). To each well of the 96-hole plates, 100 μL of Tris buffer (20 mM, pH 8.5) containing 1% Triton X-100 was added and allowed to stand for 30 minutes to dissolve cells. With respect to 100 μL of the resulting cell solution, 100 μL of Tris buffer (1.5 M, containing 1 mM of $ZnCl_2$ and 1 mM of $MgCl_2$, pH 8.5) containing 7.5 mM of p-nitrophenyl phosphate (purchased from Wako Junyaku Kogyo, Japan) were added. Increase in absorbency at 405 nm was measured to determine the alkaline phosphatase activity in the cell solution. The concentration of protein in the cell solution was also determined using a BCA assay kit (produced by Pierce).

While the alkaline phosphatase activity in the blank wells was 0.24±0.11 nmol/min·mg-protein, the alkaline phosphatase activity in the wells with the solidified peptides of Examples 1, 2, 3, 4 and 5 was 1.3±0.9 nmol/min·mg-protein, 1.5±0.6 nmol/min·mg-protein, 1.5±0.8 nmol/min·mg-protein, 1.7±0.1 nmol/min·mg-protein and 0.61±0.07 nmol/min·mg-protein, respectively.

On the other hand, in the wells to which the human recombinant BMP-2 was added, the alkaline phosphatase activity was 1.7±0.4 nmol/min·mg-protein. The peptide of Examples 1 to 4 caused remarkable increases in the alkaline phosphatase activity which were comparable to the human recombinant BMP-2.

By comparison with known sequences of the BMP family, it was estimated from the results of Example 5 that peptide STLY had good effect on the alkaline phosphatase activity.

Example 6

Ethylenediamine (EDA, produced by Wako Junyaku Kogyo, Japan), 0.6 g (10 mmol), dissolved in 10 mL of methanol was dropped into 150 mL of methanol in which 2.3 g (20 mmol) of N-hydroxysuccinimide (HOSu, produced by KK Peptide Kenkyusho, Japan) had been dissolved, while stirring at room temperature. After dropping, the mixture was stirred for another one hour. Precipitated crystals were taken by filtration and dried under reduced pressure, to obtain 2.6 g (a yield of about 90%) of ethylenediamine 2N-hydroxysuccinimide salt (EDA.2HOSu).

EDA.2HOSu, 66 mg, and 1-ethyl-3-(3-dimethylaminopropyl)-carbodiimide hydrochloride (WSCD.HCl, produced by KK Peptide Kenkyusho), 0.48g, were dissolved in 30 mL of 1 wt % aqueous solution of sodium alginate (produced by Funakoshi Kabushiki Kaisha, viscosity 550 cp, M/G ratio:1.0). The resulting mixture was cast on a 10 cm×10 cm Teflon-coated aluminum tray and allowed to stand at 25° C. for 48 hours, to obtain a covalently crosslinked gel of alginate.

The gel was sufficiently washed with water for injection (produced by Otsuka Seiyaku) in which 2.5 mM of $CaCl_2$ and 143 mM of NaCl had been dissolved and then washed only with the water for injection. The alginate gel after washing was freeze-dried to obtain a white sponge-like gel.

The resulting sponge-like gel, 0.2g, was immersed in 4 mL of dimethylformamide, to which 6 mg of N-hydroxysuccinimide and 10 mg of WSCD.HCl were added, and shook at room temperature overnight. The sponge-like gel was well washed with methanol and dimethylformamide, to which 1 mL of dimethylformamide solution containing 13 mg of the peptide obtained in Example 2 and 0.86 μL of diisopropylethylamine were added, and shook at room temperature overnight. The resulting gel was well washed with methanol and ethanol, to obtain an osteogenetic accelerator in which the peptide of Example 2 was attached to the gel.

Test Example 2

Intramuscular Implant Test on Rats

The osteogenetic accelerator obtained in Example 6, 0.01 g, was implanted in crural muscle of six-week-old male Wistar rats (purchased from Charles River Japan Inc). After four weeks, peripheral tissue including implant sites was taken out and subjected to tissue staining.

As a result, von Kossa staining revealed that calcium obviously deposited on implant sites. As a control, a sponge-like gel not having the attached peptide was implanted on the opposite side of the identical rats, where deposition of calcium was not recognized at all through the von Kossa staining.

Test Example

Deficient Tibial Bone Site Implant Test on Rats

The osteogenetic accelerator obtained in Example 6, 0.01 g, was implanted in circular deficient sites of about 3 mm diameter which had been artificially formed in tibiae of six-week-old male Wistar rats (purchased from Charles River Japan Inc).

Four weeks after implantation, tissue including the implant sites was taken out and subjected to tissue staining. Formation of neogenetic bone was obviously observed. As control, a sponge-like gel not having the attached peptide was implanted on the opposite side of the identical rats, where a trace of neogenetic bone was recognized.

According to the present invention, provided are a peptide having the osteogenetic activity and an osteogenetic accelerator containing the peptide as an active ingredient.

Since the peptide and the osteogenetic accelerator have low toxicity and excellent osteogenetic activity, they are useful for treating fractures, suppressing reduction in bone substance involved with osteoporosis and periodontal diseases and preventing fractures associated with osteoporosis and rheumatoid arthritis.

What is claimed is:

1. A peptide having an osteogenetic activity having amino acid sequences SEQ ID NO:1 and SEQ ID No:2 combined to each other with or without intervention of 1 to 10 amino acid residues which are, the same or different, selected from Asn, Cys, Pro, Gly, Ala, Val, Leu, Ile, Ser, Thr, Glu, Asp, Lys and Tyr.

2. A peptide having an osteogenetic activity having amino acid sequences SEQ ID NO:1, SEQ ID No:2 and SEQ ID No:3 combined to one another with or without intervention of 1 to 10 amino acid residues which are, the same or different, selected from Asn, Cys, Pro, Gly, Ala, Val, Leu, Ile, Ser, Thr, Glu, Asp, Lys and Tyr.

3. A peptide according to claim 1, wherein the amino acid sequence represented by SEQ ID NO:1 is located at a C terminal.

4. A peptide according to claim 1, which is one of amino acid sequences represented by SEQ ID NO: 4 to SEQ ID NO: 6, or one of amino acid sequences represented by SEQ ID NO: 4 to SEQ ID NO: 6 which has an amide group at a C terminal.

5. A peptide according to claim 1 having amino acid sequences SEQ ID NO:1, SEQ ID No:2 and SEQ ID No:3 combined to one another with or without intervention of 1 to 10 amino acid residues which are, the same or different, selected from Asn, Cys, Pro, Gly, Ala, Val, Leu, Ile, Ser, Thr, Glu, Asp, Lys and Tyr.

6. An osteogenetic accelerator containing a peptide as set forth in claim 1 as an active ingredient, wherein said osteogenetic accelerator accelerates osteogenetic activity.

7. An osteogenetic accelerator according to claim 6, wherein the peptide is attached to a carrier.

* * * * *

SEQUENCE LISTING

<160> NUMBER OF SEQ ID NOS: 7

<210> SEQ ID NO 1
<211> LENGTH: 4
<212> TYPE: PRT
<213> ORGANISM: Artificial Sequence
<220> FEATURE:
<223> OTHER INFORMATION: Description of Artificial Sequence: The sequence
      has osteogenetic function.

<400> SEQUENCE: 1

Ser Thr Leu Tyr
1

<210> SEQ ID NO 2

```
<211> LENGTH: 5
<212> TYPE: PRT
<213> ORGANISM: Artificial Sequence
<220> FEATURE:
<223> OTHER INFORMATION: Description of Artificial Sequence:The sequence
      has osteogenetic function.

<400> SEQUENCE: 2

Lys Ile Pro Lys Ala
1               5

<210> SEQ ID NO 3
<211> LENGTH: 9
<212> TYPE: PRT
<213> ORGANISM: Artificial Sequence
<220> FEATURE:
<223> OTHER INFORMATION: Description of Artificial Sequence:The sequence
      has osteogenetic function.

<400> SEQUENCE: 3

Ser Val Pro Thr Glu Leu Ser Ala Ile
1               5

<210> SEQ ID NO 4
<211> LENGTH: 25
<212> TYPE: PRT
<213> ORGANISM: Artificial Sequence
<220> FEATURE:
<223> OTHER INFORMATION: Description of Artificial Sequence: The sequence
      has osteogenetic function.

<400> SEQUENCE: 4

Asn Ser Val Asn Ser Lys Ile Pro Lys Ala Cys Ser Val Pro Thr Glu
1               5                   10                  15

Leu Ser Ala Ile Ser Thr Leu Tyr Leu
            20                  25

<210> SEQ ID NO 5
<211> LENGTH: 25
<212> TYPE: PRT
<213> ORGANISM: Artificial Sequence
<220> FEATURE:
<223> OTHER INFORMATION: Description of Artificial Sequence:The sequence
      has osteogenetic function.

<400> SEQUENCE: 5

Asn Ser Val Asn Ser Lys Ile Pro Lys Ala Ser Ser Val Pro Thr Glu
1               5                   10                  15

Leu Ser Ala Ile Ser Thr Leu Tyr Leu
            20                  25

<210> SEQ ID NO 6
<211> LENGTH: 20
<212> TYPE: PRT
<213> ORGANISM: Artificial Sequence
<220> FEATURE:
<223> OTHER INFORMATION: Description of Artificial Sequence:The sequence
      has osteogenetic function.

<400> SEQUENCE: 6

Lys Ile Pro Lys Ala Ser Ser Val Pro Thr Glu Leu Ser Ala Ile Ser
1               5                   10                  15

Thr Leu Tyr Leu
            20

<210> SEQ ID NO 7
```

```
-continued

<211> LENGTH: 5
<212> TYPE: PRT
<213> ORGANISM: Artificial Sequence
<220> FEATURE:
<223> OTHER INFORMATION: Description of Artificial Sequence:The sequence
      has osteogenetic function.

<400> SEQUENCE: 7

Ser Thr Leu Tyr Leu
 1               5
```